(12) United States Patent
Kriveshko

(10) Patent No.: US 7,940,260 B2
(45) Date of Patent: May 10, 2011

(54) THREE-DIMENSIONAL SCAN RECOVERY

(75) Inventor: Ilya A. Kriveshko, Littleton, MA (US)

(73) Assignee: 3M Innovative Properties Company, Saint Paul, MN (US)

( * ) Notice: Subject to any disclaimer, the term of this patent is extended or adjusted under 35 U.S.C. 154(b) by 455 days.

(21) Appl. No.: 11/383,623

(22) Filed: May 16, 2006

(65) Prior Publication Data

US 2007/0171220 A1      Jul. 26, 2007

Related U.S. Application Data

(63) Continuation of application No. 11/337,182, filed on Jan. 20, 2006.

(51) Int. Cl.
*G06T 15/00* (2006.01)

(52) U.S. Cl. ........ 345/419; 345/427; 382/128; 382/154; 433/29; 433/33; 433/55

(58) Field of Classification Search .................. 382/154, 382/128
See application file for complete search history.

(56) References Cited

U.S. PATENT DOCUMENTS

| | | | |
|---|---|---|---|
| 4,837,732 A | 6/1989 | Brandestini et al. | |
| 6,012,458 A | 1/2000 | Mo et al. | |
| 6,014,473 A | 1/2000 | Hossack et al. | |
| 6,099,314 A | 8/2000 | Kopelman et al. | |
| 6,201,541 B1 | 3/2001 | Shalom et al. | |
| 6,364,660 B1 | 4/2002 | Durbin et al. | |
| 6,542,249 B1 | 4/2003 | Kofman et al. | |
| 6,594,539 B1 * | 7/2003 | Geng ........................... 700/117 | |
| 6,648,640 B2 | 11/2003 | Rubbert et al. | |
| 6,701,006 B2 | 3/2004 | Moore et al. | |
| 6,819,318 B1 | 11/2004 | Geng | |
| 6,834,119 B2 | 12/2004 | Chen | |
| 6,920,242 B1 | 7/2005 | Moore et al. | |
| 6,974,964 B1 * | 12/2005 | Wang ....................... 250/559.29 | |
| 7,010,150 B1 | 3/2006 | Pfeiffer et al. | |
| 7,061,485 B2 * | 6/2006 | Tanguay et al. ............... 345/419 |
| 7,245,753 B2 * | 7/2007 | Squilla et al. ................. 382/128 |
| 2002/0050988 A1 * | 5/2002 | Petrov et al. .................. 345/418 |
| 2004/0073417 A1 * | 4/2004 | Rubbert et al. ................. 703/11 |

(Continued)

FOREIGN PATENT DOCUMENTS

EP      0837659 B1      11/1999

(Continued)

OTHER PUBLICATIONS

"Invitation to Pay Additional Fees", *PCT Search Report 1,* (Jul. 20, 2007),All Pages.

(Continued)

*Primary Examiner* — Xiao M Wu
*Assistant Examiner* — Phi Hoang

(57) ABSTRACT

A scanning system that acquires three-dimensional images as an incremental series of fitted three-dimensional data sets is improved by testing for successful incremental fits in real time and providing a variety of visual user cues and process modifications depending upon the relationship of newly acquired data to previously acquired data. The system may be used to aid in error-free completion of three-dimensional scans. The methods and systems described herein may also usefully be employed to scan complex surfaces including occluded or obstructed surfaces by maintaining a continuous three-dimensional scan across separated subsections of the surface. In one useful dentistry application, a full three-dimensional surface scan may be obtained for two dental arches in occlusion.

33 Claims, 7 Drawing Sheets

U.S. PATENT DOCUMENTS

| | | |
|---|---|---|
| 2004/0189686 A1 | 9/2004 | Tanguay, Jr. et al. |
| 2004/0197727 A1* | 10/2004 | Sachdeva et al. ............... 433/24 |
| 2004/0211836 A1* | 10/2004 | Patel et al. ............... 235/462.11 |
| 2005/0069188 A1* | 3/2005 | Rubbert et al. ............... 382/128 |
| 2005/0089213 A1* | 4/2005 | Geng ............................ 382/154 |
| 2006/0269896 A1* | 11/2006 | Liu et al. .......................... 433/29 |
| 2007/0236494 A1 | 10/2007 | Kriveshko |

FOREIGN PATENT DOCUMENTS

| | | |
|---|---|---|
| WO | WO-0008415 A1 | 2/2000 |

OTHER PUBLICATIONS

"International Search Report", *PCT Search Report 2,* (Oct. 16, 2007),All Pages.

\* cited by examiner

THREE-DIMENSIONAL SCAN RECOVERY

RELATED APPLICATIONS

This application is a continuation of commonly-owned U.S. application Ser. No. 11/337,182, filed on Jan. 20, 2006, the entire contents of which is incorporated herein by reference.

BACKGROUND

1. Field of the Invention

The invention relates to three-dimensional scanning, and more particularly to techniques for resuming a three-dimensional scan after losing data acquisition.

2. Description of the Related Art

A wide range of techniques exist for acquiring three-dimensional data from a subject. These techniques range from techniques using structured laser illumination or other controlled stimulus (such as x-rays, ultrasound, or magnetic resonance) to techniques that operate directly on video data captured from one or more cameras. While many criteria can be devised for sorting and comparing these techniques, one broad category employs continuous scanning in which incremental three-dimensional data is acquired and assembled into a full three-dimensional model.

In this latter category, regardless of the particular sensing technology, a scanning process can be divided into abstract steps of incremental data capture, incremental derivation of three-dimensional data, and registration of the incremental data to a common coordinate system. The final registration step brings the incremental data together into a single three-dimensional model of a scan subject. Typical implementations separate acquisition from registration, with registration being performed in a post-processing step after completion of the data acquisition. While this permits relatively exhaustive processing, it poses a significant disadvantage because accuracy and completeness of the overall scan cannot be evaluated until after the scan has been terminated. Unrecoverable errors or gaps in incremental data cannot be identified and fixed without initiating a new scan—possibly a full scan to completely replace the defective results. In commercial applications, this may create delays and inconvenience that increase the effective cost of scanning.

In certain instances, recovery of lost or unusable scan segments may be addressed by using robotics, independent references, or other techniques that can reliably position a scanning device within a global coordinate system. In addition to imposing further equipment costs, this approach can only be used to continue a previous scan if the subject of the scan has also retained its position and orientation within the same global coordinate system.

There remains a need for processing techniques that identify and aid in recovery from errors in incremental scans. There also remains a need for real time feedback systems to support recovery from a lost scanning sequence while the scan is in progress.

SUMMARY

A scanning system that acquires three-dimensional images as an incremental series of fitted three-dimensional data sets is improved by testing for successful incremental fits in real time and providing a variety of visual user cues and process modifications depending upon the relationship of newly acquired data to previously acquired data. The system may be used to aid in error-free completion of three-dimensional scans. The methods and systems described herein may also usefully be employed to scan complex surfaces including occluded or obstructed surfaces by maintaining a continuous three-dimensional scan across separated subsections of the surface. In one useful dentistry application, a full three-dimensional surface scan may be obtained for two dental arches in occlusion.

In one aspect, a method disclosed herein may include acquiring three-dimensional surface data from a subject as a sequence of three-dimensional images, each one of the sequence of three-dimensional images fitted to at least one previous one of the sequence of three-dimensional images, and acquiring an image set for a next three-dimensional image. When the image set can be converted into the next three-dimensional image and the next three-dimensional image can be fitted to the three-dimensional surface data, the three-dimensional surface data and the next three-dimensional image are superimposed onto a two-dimensional image of the subject in a display. Further, when the image set cannot be converted into the next three-dimensional image or the next three-dimensional image cannot be fitted to the three-dimensional surface data, a recover mode is entered. The recover mode may include superimposing a current two-dimensional image of the subject onto a previous two-dimensional image of the subject in the display. The two-dimensional image represents a view of the subject from a position from which one of the sequence of three-dimensional images was acquired. Additionally the current two-dimensional image represents a view of the subject from a position from which the image set was acquired. The recover mode further may include acquiring at least one subsequent three-dimensional image and test fitting it to one or more of the sequence of three-dimensional images.

The method may further include adding the next three-dimensional image to the three-dimensional surface data when the image set can be converted into the next three-dimensional image and the next three-dimensional image can be fit to the three-dimensional surface data. In the method, the previous two-dimensional image and the current two-dimension image may include video frames. The method may further include manually entering the recover mode in response to a user input. Also, the method may further include automatically entering the recover mode in response to a detection of a lost acquisition. The detection of a lost acquisition may include, for example, a detection of motion blur. The detection of lost acquisition may also include a detection of an insufficient recovery of three-dimensional data. In the method, the recover mode may include the step of highlighting a region on the subject for attempting a recovery. Also the highlighted region may include a plurality of previous ones of the sequence of three-dimensional images. The recover mode may include the step of test fitting at least one subsequent three-dimensional image to one or more additional images acquired during the recover mode and test fitting may include selecting a reference image from the sequence of three-dimensional images based on a suitability for test fitting. The suitability for test fitting may be based upon an entropy of image data in the previous three-dimensional image. Also, the suitability for test fitting may be based upon an amount of three-dimensional data in the previous three-dimensional image. Also, or instead, the suitability for test fitting may be based upon a placement of three-dimensional data within a range and a field of view of an imaging device. Determining the suitability for test fitting may be based upon a temporal proximity of the at least one subsequent three-dimensional image to one or more of the sequence of three-dimensional images. Determining the suitability for test fitting may be based upon a spatial proximity of the at least one subsequent three-dimensional image to one or more of the sequence of three-dimensional images. The recover mode may include the step of manually selecting one or more of the sequence of three-dimensional images. The recover mode may also include selecting a reference image from a beginning or an end of the sequence of three-dimensional images.

In another aspect, a method is disclosed herein may include providing three-dimensional surface data for a subject, and acquiring an image set for a three-dimensional image of the subject. When the image set cannot be fitted to the three-dimensional surface data, the method may enter a landing mode which may include superimposing a current two-dimensional image of the subject onto a previous two-dimensional image of the subject in the display, the current two-dimensional image representing a view of the subject from a position from which the image set was acquired, and the previous two-dimensional image representing a view of the subject from which at least a portion of the three-dimensional surface data was acquired; acquiring at least one subsequent three-dimensional image; fitting the at least one subsequent three-dimensional image to a second three-dimensional surface reconstruction; and test fitting the at least one subsequent three-dimensional image to the three-dimensional surface data. When the image set can be fitted to the three-dimensional surface data, the method superimposes the three-dimensional surface data and the next three-dimensional image onto a two-dimensional image of the subject in a display and adds the second three-dimensional surface reconstruction to the three-dimensional surface data.

In the method, the previous two-dimensional image and the current two-dimension image may include video frames. The method may further include manually entering the landing mode in response to a user input. In the landing mode, the method may include highlighting a region on the subject for attempting a landing. The highlighted region may include a portion of the three-dimensional surface data. Test fitting may include selecting a reference image from the three-dimensional surface data based on the reference image's suitability for test fitting. Suitability for testing may be based on any one or more of the following: entropy of image data in the previous three-dimensional image, amount of three-dimensional data in the previous three-dimensional image, placement of three-dimensional data within a range and a field of view of an imaging device, and spatial proximity of the image set to a portion of the three-dimensional surface data. The method may further include manually selecting a region of the three-dimensional surface data for test fitting. Test fitting may include selecting a reference image from a beginning or an end of a sequence of three-dimensional images used to construct the three-dimensional surface data. The previous two-dimensional image and the current two-dimension image may include video frames. The method may further include manually entering the recover mode in response to a user input. Additionally, the method may further include manually selecting a region from the three-dimensional surface data for test fitting.

In another aspect, a system is disclosed herein may include a scanning device that acquires three-dimensional surface data from a subject as a sequence of three-dimensional images, each one of the sequence of three-dimensional images fitted to at least one previous one of the sequence of three-dimensional images. The scanning device may include an acquisition mode in which one or more additional three-dimensional images are acquired and added to the three-dimensional surface data. Additionally the device may include a recovery mode in which one or more additional three-dimensional images are test fit to one or more of the sequence of three-dimensional images to recover the acquisition mode, and a display may be adapted to provide one or more visual indicators distinguishing between the acquisition mode and the recovery mode.

In the system, the display may be further adapted to provide guidance to an operator in manipulating the subject in the recovery mode.

In another aspect, a method is disclosed herein including performing a first acquisition of a first set of three-dimensional data from a first subject, placing a second subject in a fixed orientation relative to the first subject, and performing a second acquisition of a second set of three-dimensional data starting at a location on a surface of the first subject and including at least a portion of the second subject. In the method, the first subject and the second subject each may be a rigid body.

In the method, the location on the surface of the first subject may include a plurality of spatially proximate ones of a sequence of three-dimensional images used to derive the three-dimensional data from the first subject. Also, in the method, the location on the surface of the first subject may include a plurality of temporally proximate ones of a sequence of three-dimensional images used to derive the three-dimensional data from the first subject. Alternatively, in the method, the first subject may include a first dental arch. At least a portion of the second set of three-dimensional data may be fitted to at least a portion of the first set of three-dimensional data to provide a unified set of three-dimensional data.

The method may further include terminating the second acquisition at a location on a surface of the second subject, removing the first subject, and performing a third acquisition of three-dimensional data starting at the location on the surface of the second subject. The location on the surface of the second subject may include a plurality of spatially proximate ones of a sequence of three-dimensional images used to derive the three-dimensional data from the second subject. Alternatively, the location on the surface of the second subject may include a plurality of temporally proximate ones of the sequence of three-dimensional images used to derive the three-dimensional data from the second subject.

The method may further include combining the first set of three-dimensional data, the second set of three-dimensional data, and the third set of three-dimensional data into a unified set of three-dimensional data. In the method, the second subject may include a second dental arch, and the fixed orientation may include the first dental arch and the second dental arch in occlusion.

In another aspect, a system disclosed herein may include an acquisition means for performing a first acquisition of a first set of three-dimensional data from a first subject, and a positioning means for placing a second subject in a fixed orientation relative to the first subject. In the system, the acquisition means may include a means for performing a second acquisition of a second set of three-dimensional data starting at a location on a surface of the first subject and including at least a portion of the second subject. In the system, the first subject and the second subject each may be a rigid body.

In the system, the location on the surface of the first subject may include a plurality of spatially proximate ones of a sequence of three-dimensional images used to derive the three-dimensional data from the first subject. Alternatively, the location on the surface of the first subject may include a plurality of temporally proximate ones of a sequence of three-dimensional images used to derive the three-dimensional data from the first subject. The first subject may include a first dental arch. At least a portion of the second set of three-dimensional data may be fitted to at least a portion of the first set of three-dimensional data to provide a unified set of three-dimensional data. The system may further include a control means for terminating the second acquisition at a location on a surface of the second subject, the positioning means may include a means for removing the first subject; and the acquisition means may include a means for performing a third acquisition of three-dimensional data starting at the location on the surface of the second subject. The location on the surface of the second subject may include a plurality of spatially proximate ones of a sequence of three-dimensional images used to derive the three-dimensional data from the second subject. Alternatively, the location on the surface of the second subject may include a plurality of temporally proximate ones of the sequence of three-dimensional images used to derive the three-dimensional data from the second subject. The system may further include a computing means for combining the first set of three-dimensional data, the second set of three-dimensional data, and the third set of three-dimensional data into a unified set of three-dimensional data. In the system, the second subject may include a second dental arch, and the fixed orientation may include the first dental arch and the second dental arch in occlusion.

In another aspect, a method disclosed herein may include placing a first subject in a fixed orientation relative to a second subject, acquiring a first set of three-dimensional data including a first portion of the first subject and a first portion of the second subject, acquiring a second set of three-dimensional data from the first subject in isolation starting at a location on a surface of the first subject and including a second portion of the first subject different from the first portion of the first subject, and combining the first set of three-dimensional data with the second set of three-dimensional data.

In the method, the first subject and the second subject may be a rigid body. Alternatively, the first subject may include a first dental arch. The location on the surface of the first subject may include a plurality of spatially proximate ones of a sequence of three-dimensional images used to derive the three-dimensional data from the first subject. Alternatively, the location on the surface of the first subject may include a plurality of temporally proximate ones of a sequence of three-dimensional images used to derive the three-dimensional data from the first subject. The method may further include acquiring a third set of three-dimensional data from the second subject in isolation starting at a location on a surface of the second subject and including a second portion of the second subject, and combining the third set of three-dimensional data with the first and second sets of three-dimensional data. The location on the surface of the second subject may include a plurality of spatially proximate ones of a sequence of three-dimensional images used to derive the three-dimensional data from the second subject. Alternatively, the location on the surface of the second subject may include a plurality of temporally proximate ones of the sequence of three-dimensional images used to derive the three-dimensional data from the second subject. The second subject may include a second dental arch, and the fixed orientation may include the first dental arch and the second dental arch in occlusion.

In another aspect, a method disclosed herein may include providing a first set of three-dimensional data from a subject, scanning the subject to acquire one or more additional three-dimensional images, test fitting each one of the one or more additional three-dimensional images to the set of three dimensional data, and upon a successful fit, adding the one or more additional three-dimensional images to the set of three-dimensional data.

The method may include fitting each new one of the one or more additional three-dimensional images to one another to provide a second set of three-dimensional data, and upon a successful fit, adding the second set of three-dimensional data to the first set of three-dimensional data. The three-dimensional data may include three-dimensional surface data. Alternatively, the one or more additional three-dimensional images may include surface data derived from two-dimensional image sets of the subject. In the method, the set of three-dimensional data may include three-dimensional surface data acquired from a subject as a sequence of three-dimensional images, each one of the sequence of three-dimensional images fitted to at least one previous one of the sequence of three-dimensional images.

In another aspect, a system disclosed herein may include a storage means for providing a first set of three-dimensional data from a subject, an acquisition means for scanning the subject to acquire one or more additional three-dimensional images, and a computing means for test fitting each one of the one or more additional three-dimensional images to the set of three dimensional data. The computing means may further include a means for detecting a successful fit and, upon detecting a successful fit, may add the one or more additional three-dimensional images to the set of three-dimensional data.

In the system, the computing means may include a means for fitting each new one of the one or more additional three-dimensional images to one another to provide a second set of three-dimensional data, and upon a successful fit, may add the second set of three-dimensional data to the first set of three-dimensional data. In the system, the three-dimensional data may include three-dimensional surface data. Alternatively in the system, the one or more additional three-dimensional images may include surface data derived from two-dimensional image sets of the subject. The set of three-dimensional data may include three-dimensional surface data acquired from a subject as a sequence of three-dimensional images, each one of the sequence of three-dimensional images may be fitted to at least one previous one of the sequence of three-dimensional images.

In another aspect, a computer program product disclosed herein may include computer executable code which may be embodied on a computer readable medium that, when executing on one or more computing devices, performs the steps of providing a first set of three-dimensional data from a subject, scanning the subject to acquire one or more additional three-dimensional images, test fitting each one of the one or more additional three-dimensional images to the set of three dimensional data, and upon a successful fit, adding the one or more additional three-dimensional images to the set of three-dimensional data.

The computer program product may further include code to perform the steps of fitting each new one of the one or more additional three-dimensional images to one another to provide a second set of three-dimensional data, and upon a successful fit, adding the second set of three-dimensional data to the first set of three-dimensional data.

In the computer program product, the three-dimensional data may include three-dimensional surface data. Alternatively, in the computer program product, the one or more additional three-dimensional images may include surface data derived from two-dimensional image sets of the subject. The set of three-dimensional data may include three-dimensional surface data acquired from a subject as a sequence of three-dimensional images, each one of the sequence of three-dimensional images may be fitted to at least one previous one of the sequence of three-dimensional images.

In another aspect, a method disclosed herein may include providing a first set of three-dimensional data from a subject, scanning the subject to acquire one or more additional three-dimensional images, test fitting each one of the one or more additional three-dimensional images to the first set of three-dimensional data in real time, and providing real time visual feedback to a user relating to the test fitting.

In the method, providing real time visual feedback may include superimposing the first set of three-dimensional data and the one or more additional three-dimensional images on a video image of the subject when a test fit is successful. Providing real time visual feedback may include displaying one or more navigation cues when a test fit is unsuccessful. When the test fitting is unsuccessful, the method may further include fitting each new one of the one or more additional three-dimensional images to one another to provide a second set of three-dimensional data. Upon a successful fit, the method may further include adding the second set of three-dimensional data to the first set of three-dimensional data. The three-dimensional data may include three-dimensional surface data. The one or more additional three-dimensional images may include surface data derived from two-dimensional image sets of the subject. Additionally, the set of three-dimensional data may include three-dimensional surface data acquired from a subject as a sequence of three-dimensional images, each one of the sequence of three-dimensional images fitted to at least one previous one of the sequence of three-dimensional images.

In another aspect, a system disclosed herein may include a storage means for providing a first set of three-dimensional data from a subject, an acquisition means for scanning the subject to acquire one or more additional three-dimensional images, a computing means for test fitting each one of the one or more additional three-dimensional images to the first set of three-dimensional data in real time, and a display means for providing real time visual feedback to a user relating to the test fitting.

In the system, providing real time visual feedback may include superimposing the first set of three-dimensional data and the one or more additional three-dimensional images on a video image of the subject when a test fit is successful. Alternatively, providing real time visual feedback may include displaying one or more navigation cues when a test fit is unsuccessful. The computing means may include means for, when the test fitting is unsuccessful, fitting each new one of the one or more additional three-dimensional images to one another to provide a second set of three-dimensional data, and upon a successful fit, adding the second set of three-dimensional data to the first set of three-dimensional data. Alternatively, the three-dimensional data may include three-dimensional surface data. The one or more additional three-dimensional images may include surface data derived from two-dimensional image sets of the subject. The set of three-dimensional data may include three-dimensional surface data acquired from a subject as a sequence of three-dimensional images, each one of the sequence of three-dimensional images fitted to at least one previous one of the sequence of three-dimensional images.

In another aspect, a computer program product disclosed herein may include computer executable code embodied on a computer readable medium that, when executing on one or more computing devices, performs the steps of providing a first set of three-dimensional data from a subject, scanning the subject to acquire one or more additional three-dimensional images, test fitting each one of the one or more additional three-dimensional images to the first set of three-dimensional data in real time, and providing real time visual feedback to a user relating to the test fitting.

In the computer program product, providing real time visual feedback may include superimposing the first set of three-dimensional data and the one or more additional three-dimensional images on a video image of the subject when a test fit is successful. Alternatively, providing real time visual feedback may include displaying one or more navigation cues when a test fit is unsuccessful. The computer program product may further include computer code that performs the steps of, when the test fitting is unsuccessful, fitting each new one of the one or more additional three-dimensional images to one another to provide a second set of three-dimensional data, and upon a successful fit, adding the second set of three-dimensional data to the first set of three-dimensional data. The three-dimensional data may include three-dimensional surface data. The one or more additional three-dimensional images may include surface data derived from two-dimensional image sets of the subject. The set of three-dimensional data may include three-dimensional surface data acquired from a subject as a sequence of three-dimensional images, each one of the sequence of three-dimensional images fitted to at least one previous one of the sequence of three-dimensional images.

BRIEF DESCRIPTION OF THE FIGURES

The invention and the following detailed description of certain embodiments thereof may be understood by reference to the following figures.

DETAILED DESCRIPTION

Described below is a technique for providing real time visual feedback to a user operating an incremental three-dimensional scanning device. However, it will be appreciated that the inventive concepts disclosed herein are not limited to such applications, and may be usefully employed in a number of imaging applications. For example, while visible light, video-based systems are described in some detail, the techniques described herein may be usefully applied to other imaging modalities based on, for example, x-rays, infrared or ultraviolet light, ultrasound, laser light, and so forth. As another example, the systems described herein may be usefully employed in two-dimensional imaging systems or other applications where user feedback and correction might be augmented by real time visual feedback. As a further example, the systems and methods described herein may be employed in an automated, robotic system to automate rescanning of regions of a subject where incremental image data has been lost or degrades in quality below a predetermined threshold. All such variations and alternative embodiments as would be apparent to one of ordinary skill in the art are intended to fall within the scope of this disclosure.

In the following description, the term "image" generally refers to a set of two-dimensional pixels forming a two-dimensional view of a subject within an image plane. The term "image set" generally refers to a set of related two dimensional images that might be resolved into three-dimensional data. The term "point cloud" generally refers to a set of three-dimensional points forming a three-dimensional view of the subject reconstructed from a number of two-dimensional views. In a three-dimensional image capture system, a number of such point clouds may also be registered and combined into an aggregate point cloud constructed from images captured by a moving camera. Thus it will be understood that pixels generally refer to two-dimensional data and points generally refer to three-dimensional data, unless another meaning is specifically indicated or clear from the context.

Figure 1:
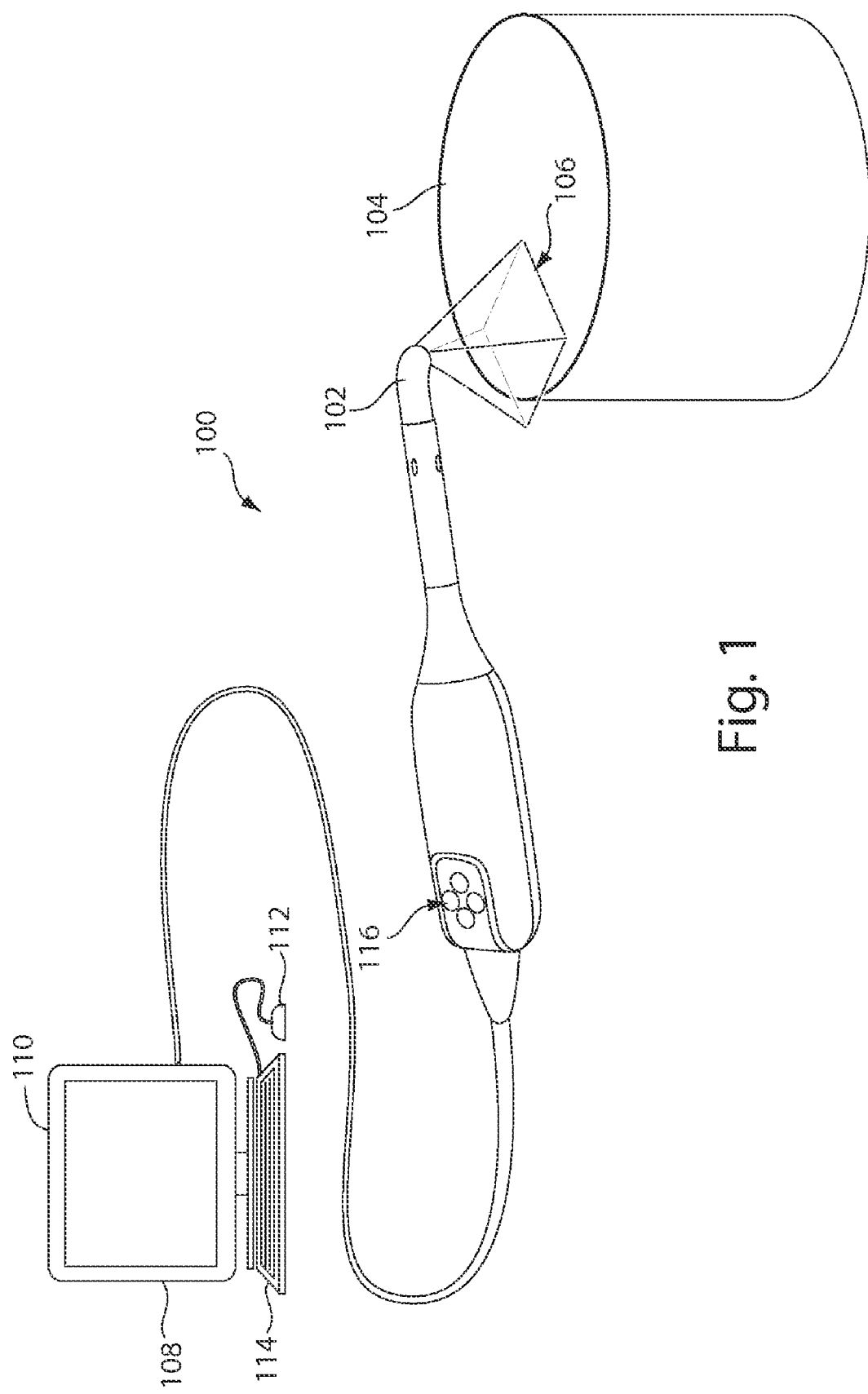
FIG. 1 shows an image capture system.

FIG. 1 shows an image capture system. In general, the system 100 may include a scanner 102 that captures images of a subject 104 within an image plane 106, and forwards the images to a computer 108, which may include a display 110 and one or more user input devices such as a mouse 112 or a keyboard 114.

The scanner 102 may include any camera or camera system suitable for capturing images from which a three-dimensional point cloud may be recovered. For example, the camera 102 may employ a multi-aperture system as disclosed, for example, in U.S. Pat. Pub. No. 20040155975 to Hart et al., the entire contents of which is incorporated herein by reference. While Hart discloses one multi-aperture system, it will be appreciated that any multi-aperture system suitable for reconstructing a three-dimensional point cloud from a number of two-dimensional images may similarly be employed. In one multi-aperture embodiment, the scanner 102 may include a plurality of apertures including a center aperture positioned along a center optical axis of a lens and any associated imaging hardware. The scanner 102 may also, or instead, include a stereoscopic, triscopic or other multi-camera or other configuration in which a number of cameras or optical paths are maintained in fixed relation to one another to obtain two-dimensional images of an object from a number of slightly different perspectives. The scanner 102 may include suitable processing for deriving a three-dimensional point cloud from an image set or a number of image sets, or each two-dimensional image set may be transmitted to an external processor such as contained in the computer 108 described below. In other embodiments, the scanner 102 may employ structured light, laser scanning, direct ranging, or any other technology suitable for acquiring three-dimensional data, or two-dimensional data that can be resolved into three-dimensional data. In one embodiment, the scanner 102 is a handheld, freely positionable probe having at least one user input device, such as a button, lever, dial, thumb wheel, switch, or the like, for user control of the image capture system 100 such as starting and stopping scans.

Although not shown in FIG. 1, it will be appreciated that a number of supplemental lighting systems may be usefully employed during image capture. For example, environmental illumination may be enhanced with one or more spotlights illuminating the subject 104 to speed image acquisition and improve depth of field (or spatial resolution depth). The scanner 102 may also, or instead, include a strobe, flash, or other light source to supplement illumination of the subject 104 during image acquisition.

The subject 104 may be any object, collection of objects, portion of an object, or other subject matter. While illustrated in FIG. 1 as a simple geometric form, the subject 104 may include much more complex surfaces, and any number of separate elements. For example, in a dental imaging application, the subject 104 may include a tooth, a quadrant of teeth, or a full collection of teeth including two opposing arches from which a virtual dental impression is desired. The subject 104 may also, or instead, include a dental prosthesis such as an inlay, a crown, or any other dental prosthesis, implant, or the like. The subject 104 may include a dental model, such as a plaster cast, wax-up, impression, or negative impression of a tooth, teeth, soft tissue, or some combination of these. In certain instances, an optical or textured imaging agent may be applied to surfaces of the subject 104 to improve capture of three dimensional points. In other embodiments, the subject 104 may be a human head, or a portion thereof, from which a three-dimensional model is desired for custom fitting of a hearing aid, eyeglasses, goggles, or the like. In other embodiments, the subject 104 may be a physical model of an object for use in digital animation, such as a miniature, physical model for use in a three-dimensional digital animation process. From the preceding examples, it will be apparent that a system using the techniques described herein may be suitably adapted to a wide range of applications for relatively short range, high resolution three-dimensional image acquisition. However, one skilled in the art will appreciate that suitable adaptations to the image capture system 100 may be made for a variety of other three-dimensional imaging applications based upon multi-aperture or multi-camera systems, as well as other three-dimensional imaging systems and technologies, and all such variations are intended to fall within the scope of this disclosure.

The image plane 106 may include a two-dimensional field of view of the camera 102. It will be appreciated that the term "image plane" as used in this paragraph, refers to a plane in the imaging environment rather than a plane within an optical sensor (such as film or sensors) where an image is captured. Though illustrated as a rectangle the image plane 106 may, for example, form a square, a circle, or any other geometry provided by the scanner 102. In general, the scanner 102 will have a depth of field or range of depth resolution for image acquisition within the image plane 106 determined by the physical construction of the scanner 102 and environmental conditions such as ambient light.

The computer 108 may be, for example, a personal computer or other processing device. In one embodiment, the computer 108 includes a personal computer with a dual 2.8 GHz Opteron central processing unit, 2 gigabytes of random access memory, a TYAN Thunder K8WE motherboard, and a 250 gigabyte, 10,000 rpm hard drive. This system may be operated to capture approximately 1,500 points per image set in real time using the techniques described herein, and store an aggregated point cloud of over one million points. More generally, processing capabilities of the computer 108 may vary according to the size of the subject 104, the speed of image acquisition, and the desired spatial resolution of three-dimensional points. The computer 108 may also include peripheral devices such as a keyboard 114, display 110, and mouse 112 for user interaction with the camera system 100.

The display 110 may be a touch screen display capable of receiving user input through direct, physical interaction with the display 110.

Communications between the computer 108 and the scanner 102 may use any suitable communications link including, for example, a wired connection or a wireless connection based upon, for example, IEEE 802.11 (also known as wireless Ethernet), BlueTooth, or any other suitable wireless standard using, e.g., a radio frequency, infrared, or other wireless communication medium. In medical imaging or other sensitive applications, wireless image transmission from the scanner 102 to the computer 108 may be secured. The computer 108 may generate control signals to the scanner 102 which, in addition to image acquisition commands, may include conventional camera controls such as focus or zoom.

In an example of general operation of a three-dimensional image capture system 100, the scanner 102 may acquire two-dimensional image sets while the scanner 102 is passed over a surface of the subject. The two-dimensional image sets may be forwarded to the computer 108 for derivation of three-dimensional point clouds. The three-dimensional data for each newly acquired two-dimensional image set may be derived and fitted or "stitched" to existing three-dimensional data using a number of different techniques. One useful example of such a technique is described in commonly-owned U.S. application Ser. No. 11/270,135, filed on Nov. 9, 2005, the entire contents of which is incorporated herein by reference. However, it will be appreciated that this example is not limiting, and that the principles described herein may be applied to a wide range of three-dimensional image capture systems.

From time to time in such incremental data acquisition systems, the fitting or stitch may fail for reasons described in greater detail below. In such situations, a user may be notified through visual feedback that a recover mode has been entered. In the recover mode, the system 100 may seek to reacquire the previous scan by test fitting new scan data to previously acquired data, and providing visual feedback to a user to assist in navigating back to a scan location on the subject where the re-acquisition is being attempted. In a related landing mode, a user may attempt to initiate a new scan registered or connected to an existing three-dimensional model. Similar visual feedback tools may be provided to guide a user to an appropriate scan location, and notify a user when the scan has been reacquired. These techniques are now described in greater detail, beginning with a detailed description of the processes for a stitch recovery and a landing, described with reference to FIGS. 2 and 3. The corresponding user interface is described in greater detail with reference to FIG. 4 et seq.

Figure 2:
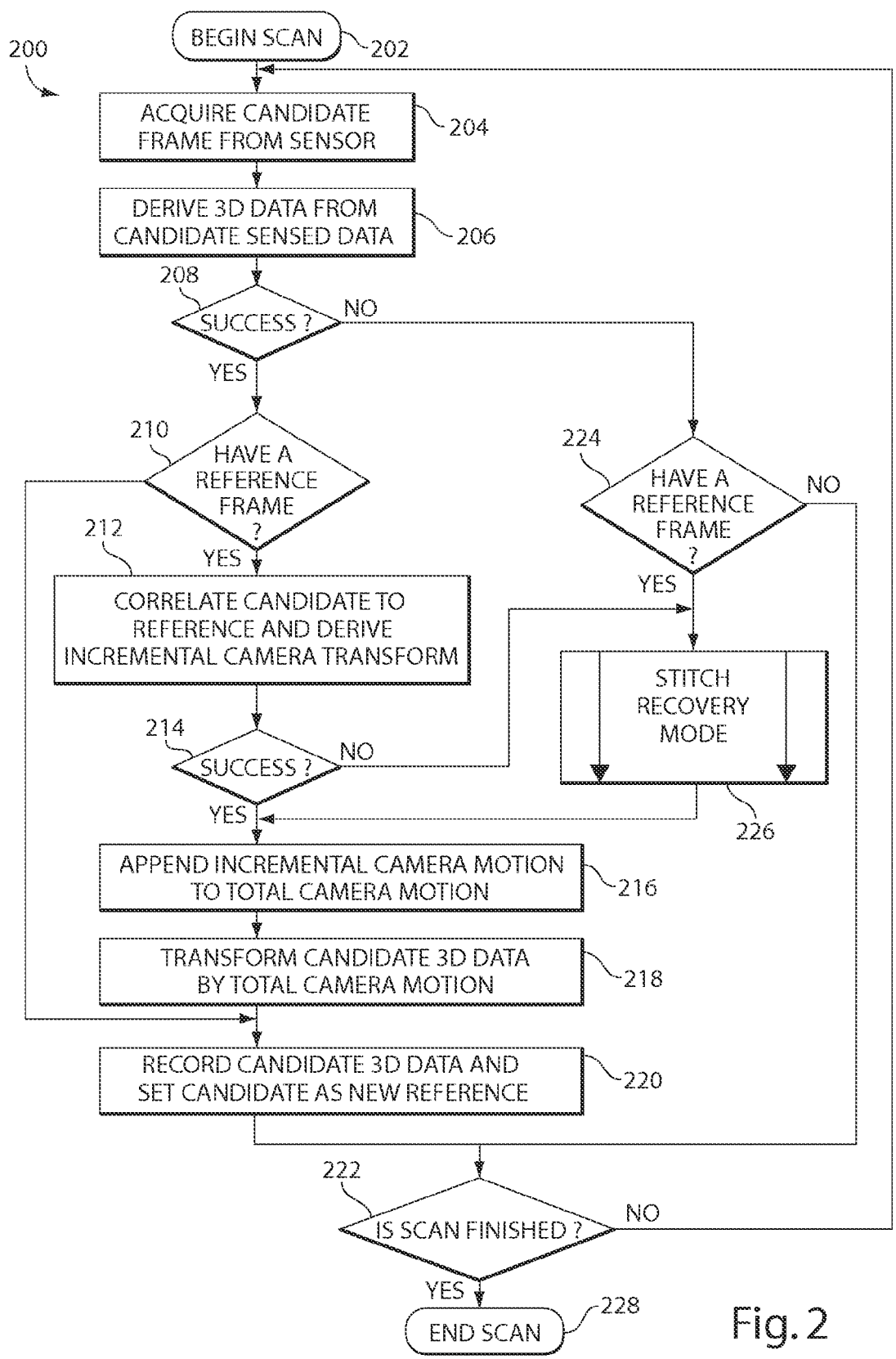
FIG. 2 shows a process for operating an image capture system.

FIG. 2 depicts a process for three-dimensional scanning. The process 200 may begin 202 by acquiring a candidate frame from a sensor, such as an image set from the scanner 102 described above, as shown in step 204. During this phase of the process 200, a video image such as a video image of the subject from a position or point of view of the scanning device, may be rendered on the display 110. This view may assist a user of the image capture system 100 in positioning the scanner 102 relative to the subject 104. In such embodiments, the view will continuously shift as the user moves the scanner 102 about the subject 104, always maintaining a visual display of the point of view of the scanner 102 on the subject 104. In other embodiments, the subject 104 may be displayed in a static, non-moving orientation within the display 110, while a visual cue may be provided within the user interface as to a position and orientation of the scanner.

As shown in step 206, three-dimensional data may be derived from the candidate frame. Stated alternatively, the two-dimensional data, such as an image set, may be converted into three-dimensional data or a three-dimensional image. As used herein, the terms three-dimensional data, three-dimensional representation, three-dimensional model, three-dimensional image, three-dimensional surface map, and the like are used interchangeably to describe the three-dimensional representation assembled from incremental scan results captured by the scanning device, or a portion thereof, unless a different meaning to these phrases is explicitly stated or clear from the context.

A number of techniques may be employed to calculate three-dimensional point values from the candidate frame. For example, stereoscopic matching techniques include probabilistic measures of image similarity such as mutual information or correlation of pixel intensities. Other types of suitable derivations include, for example, optical flow using spatial and/or temporal gradients. In a stereoscopic camera configuration, for example, the image set typically includes two images. However, three or more images may be included in an image set using a multi-aperture camera configuration, such as a three or four aperture camera, or similar camera systems. It should also be appreciated that each set of three-dimensional data need not include all, or even most, of the points that might be recovered from the candidate frame. The point cloud may, for example, be calculated from a sparse mesh of a candidate frame image set (relative to the pixel density of the original image set). This arrangement may be particularly suitable for accelerating processing in real time imaging applications. The sparse mesh may be obtained from any subset of pixels in the image set. Regular rectangular grids, for example, are particularly suited to hierarchical methods using subsampling of images. However, other meshes may be used, such as triangular, square, quadrilateral, or the like, to select regularly or irregularly spaced pixels within the image set for derivation of a point cloud. In some embodiments, a relatively sparse subset of pixel data may be employed for real time rendering and feedback, while a denser or complete version of pixel data is stored for use in a more computationally intensive post-processing step, which might yield greater accuracy and density.

It will be appreciated that three-dimensional surface data consisting of a point cloud of three-dimensional points is one type of three-dimensional data that may be readily derived from two-dimensional image sets. However, other forms of three-dimensional data may also be obtained using various techniques known in the art. This may include, for example, three-dimensional surface data consisting of a three-dimensional map of interconnected polygons, such as triangles or other regular or irregular polygons, or volumetric three-dimensional data reflecting interior as well as surface points of the subject. All such variations are intended to fall within the scope of this disclosure.

As shown in step 208, once three-dimensional data has been derived, it may be evaluated to determine whether the derivation was successful. In general, this tests the recovery of incremental data for internal consistency, rather than by comparison to the full three-dimensional model reconstructed from incremental scans. For example, movement of the scanner laterally off the subject may result in an insufficient amount of derived data, or a complete lack of derived data. Similarly, with certain imaging technologies, rapid scanner motion may cause blurring in acquired two-dimensional image sets that interferes with conversion to three-dimensional data. This motion blur may render an image set unsuitable for derivation of three-dimensional data, or reduce the quality of derived three-dimensional data. Other scanner motions, such as movement outside the scanner's physical scanning range (again, this may be technology dependent), such as too close or too far away from the subject, may result in low quality or insufficient derived three-dimensional data. Other imaging artifacts may similarly render a particular image set unsuitable (or less suitable) for deriving three-dimensional data, such as lack of texture on a surface of the subject, poor optical focus or resolution, illumination anomalies such as specularities or shadows, distortion and aberration artifacts in components in the optical path, and so forth. Other factors such as physical properties of the subject may cause deterioration of data acquisition. For example, highly reflective surfaces may interfere with three-dimensional conversion. Various quantitative measures of success may be employed, and in various embodiments, numerical thresholds may be user-specified according to a desired accuracy of the resulting three-dimensional model. If it is determined that the two-dimensional data (or other sensor data, as discussed generally above) has been successfully converted into three-dimensional data, then the process 200 may proceed to step 210. If it is determined that the two-dimensional data has not been successfully converted into three-dimensional data, then the process may proceed to step 224.

In step 210, a determination may be made as to whether there is a reference frame or image, such as a previously acquired image set or derived three-dimensional data. In one embodiment, a reference frame will always be available, except when the currently acquired frame is the first frame in a sequence. In various embodiments, different data types may be employed for comparison of incremental data, such as two-dimensional source data, converted three-dimensional data points, and so forth. However, in step 210, the process 200 is only testing for the existence of a reference frame, not the quality of the image frame. If a reference frame is present, the process 200 may proceed to step 212. If a reference frame is not present, the process 200 may proceed to step 220.

As shown in step 212, the incremental three-dimensional image data may be fitted or stitched to the existing three-dimensional model. In one embodiment, this process is performed by deriving scanner motion between positions or points of view for successive image captures. However, other techniques may be employed, such as direct fitting of features from the new three-dimensional image to the previously acquired three-dimensional model. All such techniques that might usefully be employed to register new three-dimensional data to existing three-dimensional data are intended to fall within the scope of this disclosure. Once a fit has been attempted in step 212, the process 200 may proceed to step 214.

In step 214, the fit obtained in step 212, which may be considered a test fit until accepted for addition to the previously acquired three-dimensional data, may be tested for success. This test fitting may employ any number of quantitative techniques for comparing some or all of the newly acquired three-dimensional data to the previously acquired three-dimensional data. Tests such as correlation or feature matching may be employed to obtain a confidence score or other objective measure of fitting. Further, where a quantitative limit or range is employed to measure a successful fit, the limit or range may be user-controlled either by explicit selection of a numeric fit parameter or by selection of a qualitative fit parameter (e.g., tight, moderate, loose, etc.). User evaluation and feedback may also be incorporated into a fitting algorithm, which may, for example, be in response to a frequently recurring failure to fit, or to a specific failure event. It will be appreciated that, while a single test fit is shown in step 214, any number of test fits may be performed during this step. In this manner, a number of sequentially acquired three-dimensional images used in whole or in part to constitute the three-dimensional model may each be test fitted to the newly acquired three-dimensional data. This approach may have particular utility where test fitting employs two-dimensional image set data instead of, or in addition to, any three-dimensional data derived therefrom.

In one example embodiment, a number of different reference frames (also referred to herein as reference images) may be selected for a test fit. The number of reference frames may be selected using various criteria. For example, reference frames may be selected according to temporal proximity to the new incremental data. That is, a group of most recent image sets or three-dimensional data sets may be employed for test fitting. As another example, reference frames may be selected according to spatial proximity to the new incremental data. That is, a group of image sets or three-dimensional data sets that are physically closest to the last known point on the subject may be used. Other techniques may be suitably employed for selecting candidate reference frames, either alone or in combination, including image entropy, data density, data quantity, and/or scanning parameters (such as focal distance or location within field of view). In one embodiment reference frames may be selected from a beginning of the sequence of incremental three-dimensional images used to create the three-dimensional model, such that a user may attempt reacquisition from where the original scan was initiated. In one embodiment, reference frames may be selected for an end of the sequence of incremental three-dimensional images used to create the three-dimensional model, such that a user may attempt reacquisition from where the original scan was lost. In one embodiment, a user may specifically select a point or region on the three-dimensional model for test fitting. This user selection may be used to derive a pool of candidate frames based upon the techniques described above. Manual selection will be discussed in greater detail with reference to the stitch recover mode in FIG. 3. Generally, the manual selection may be achieved through operation of the user interface to select one or more points on the existing three-dimensional model.

If the new three-dimensional data is successfully fitted to the existing three-dimensional data, then the process may proceed to step 216. If the new three-dimensional data is not successfully fitted to the existing three-dimensional data, then the process may proceed to step 226.

As shown in step 216, new or incremental three-dimensional data may be added to the three-dimensional model. In one embodiment using camera motion estimation, this step may include a rigid transformation of the incremental three-dimensional data to the coordinate system of the three-dimensional model, as depicted in step 218. However, it will be appreciated that any suitable technique for registering new three-dimensional data to existing three-dimensional data may be usefully employed in step 216, and the choice of a particular technique may vary according to the scanning technology and/or sensor data of a particular image capture system.

As shown in step 220, the new or incremental three-dimensional data may next be selected as a candidate reference frame for subsequent acquisitions of one or more sequential data sets from the scanner 102. At this point, the process 200 may proceed to step 222.

As shown in step 222, a determination may be made as to whether the scan is finished. This may include, for example, user input received through the input device 116 on the scanner 102, through the mouse 112, the keyboard 114, or, for a touch screen embodiment, through the display 110. It will be appreciated that in certain embodiments, the process 200 may be stopped at any point upon receipt of such a user input. If it is determined that the scan is finished, the process 200 may proceed to step 228 and end. If it is determined that the scan is not finished, the process may return to step 204 where a new candidate frame may be acquired from the scanner 102. In a subsequent pass through the following processing steps, the "newly acquired" three-dimensional data may be used as a reference frame for subsequent fitting steps.

As shown in step 224, when a derivation of three-dimensional data is unsuccessful (which may also be understood as a species of unsuccessful fitting, discussed with reference to step 214), the process 200 may proceed to determine whether at least one reference frame exists. If no reference frame exists, then the process may proceed to step 222, and subsequently to step 204 where a new candidate frame may be acquired. If a reference frame does exist, the process may proceed to step 226, which more generally represents a stitch recovery mode 226.

In the stitch recover mode 226 the process 200 may attempt to reacquire or resume a scan by test fitting each newly acquired data set to some portion of the three-dimensional model. During this phase, the process may optionally begin assembling a new three-dimensional model from sequential, incremental three-dimensional data sets. In this manner, once the original scan is reacquired with a successful fit to the original three-dimensional model, all of the three-dimensional data acquired during the recover mode may be immediately registered to the original three-dimensional model. Although not explicitly depicted, it will be appreciated that in certain embodiments a user may manually select the recover mode 226, such as where a scan is purposely interrupted by the user. It will be noted that the terms "reacquire" "resume" and are used interchangeably herein to refer to either scans that have been lost due to signal degradation or scans that have been explicitly stopped through user operation.

In one aspect, the process 200 described herein, and systems embodying this process, include two operating modes. In an acquisition mode, normal acquisition, conversion to three-dimensional data, and test fitting to the three-dimensional model may take place, as described generally above. In a recover mode, or in the landing mode described below, newly acquired incremental data is test fitted to the three-dimensional model, but may also be fitted to a second model so that useful three-dimensional data may continue to be acquired during the recover mode, which is described in greater detail with reference to FIG. 3.

In another aspect, visual cues or indicators may be provided to a user through the monitor 110 with respect to whether the image capture system 100 is in a recover mode or a normal acquisition mode. For example, in the normal acquisition mode, the display 110 may show a video image of the subject 104, as viewed from the scanner 102. The computer may render the three-dimensional model, which may be a three-dimensional point cloud of surface data acquired for the subject 104, superimposed on the video image. The surface data may be rendered with shading, or a wireframe or other visual techniques to visualize the three-dimensional shape of the surface data. In this mode, the user experience may be one of virtually spray painting a surface of the subject 104 with points or other surface rendering (such as polygons) that reflects the acquired three-dimensional model. In the recover (or landing) mode, the computer may render the video image of the subject 104 as viewed from the scanner 102; however, the computer 108 may remove or stop rendering the three-dimensional model. This may provide immediate user feedback that acquisition has been lost. In addition, the computer may render a previous video image of the subject 104 from a previous position of the scanner 102, in particular, a previous position or location on the subject 104 selected as a reference frame for re-acquisition, superimposed on the current video image. The superimposed video image from the previous location may be rendered in a different color, or with different opacity to provide a visual offset from the current video image. By superimposing the previous video image, as centered on the location where re-acquisition is being algorithmically test fitted, the system can provide feedback to a user that will assist the user in re-centering the scanner 102 at the desired position on the subject 104. Thus the user may be provided with visual cues as to the acquisition mode and the recover mode. The recover mode, in particular, may provide visual feedback to assist a user in re-acquiring three-dimensional data acquisition for the original three-dimensional model. It will be appreciated that other techniques may be employed, such as directional arrows or verbal cues, to coach a user back to an appropriate location relative to the subject 104. Using the computer 108 described above, the visual cues or indicators may be rendered at a video rate consistent with image capture, so that the system provides real time visual feedback to a user.

The recover mode will now be described in greater detail.

Figure 3:
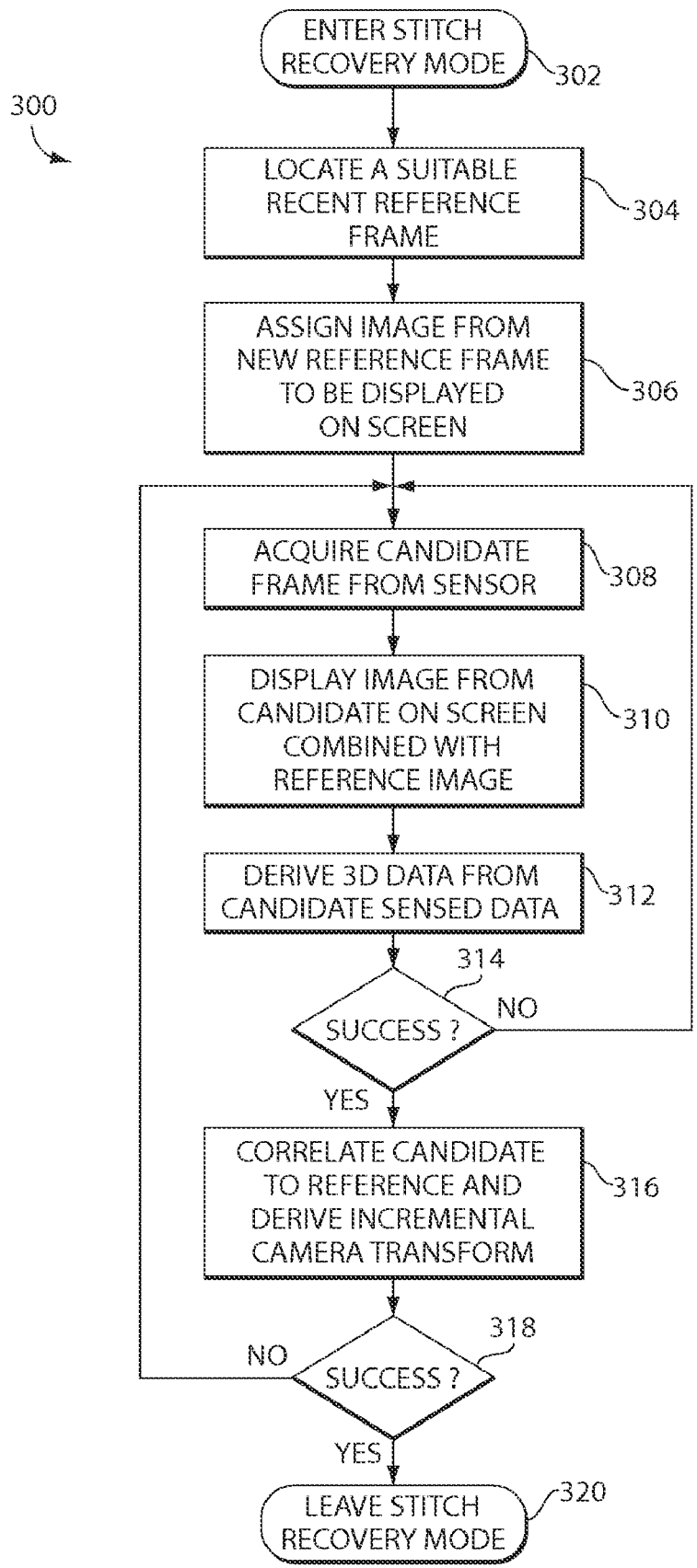
FIG. 3 shows a process for operating an image capture system.

As shown in FIG. 3, a recover mode process 300 may begin by entering a stitch recover mode 302. This may occur through any of the circumstances described above with reference to FIG. 2, including manual selection of the recover mode by a user.

As shown in step 304, a suitable reference frame may be selected. This may include one or more reference frames, which may be selected using any of the techniques described above with reference to step 214 of FIG. 2. It will be appreciated that the reference frames for the recover mode are reference frames selected from the three-dimensional model assembled during the acquisition mode of FIG. 2. After one or more reference frames have been selected, the process 300 may proceed to step 306.

As shown in step 306, a reference frame may be assigned for display. This may be a video image corresponding to one of the reference frames selected in step 304, as well as any corresponding two-dimensional or three-dimensional data suitable for use in display thereof. More generally, the content of the reference frame may vary according to a particular imaging technology and/or techniques used to fit incremental data.

As shown in step 308, a new frame of data may be acquired from the scanner 102, including a current video image.

As shown in step 310, the current video image may be displayed on the monitor 110 superimposed on a reference video image selected in step 306. The images may be superimposed on the monitor 110 as a visual indicator for the user. The reference video image may be superimposed on a current video image captured from a current position of the scanner, with each video image distinguished using a visual cue such as color, opacity, or the like. This superposition may indicate to a user both where the scanner is currently positioned and where the scanner should be positioned in order to reacquire a scan, so that a user may manipulate the scanner to a suitable position for recovery.

As shown in step 312, three-dimensional data may be derived from the new frame of data, as described for example with reference to step 206 of FIG. 2.

As shown in step 314, success of the derivation may be evaluated, as described for example with reference to step 208 of FIG. 2. If the derivation is successful, the process 300 may proceed to step 316. If the derivation is unsuccessful, the process 300 may proceed to step 308 where a new frame of data may be acquired.

As shown in step 316, the newly derived three-dimensional data may be test fitted to the reference frame(s) from the acquisition mode, using techniques such as those described above with reference to step 212 of FIG. 2.

As shown in step 318, the test fit may be evaluated for success. If new data is successfully test fitted to the reference frame(s), the process 300 may proceed to step 320 and exit the recover mode. If the new data is not successfully test fitted to the reference frame(s), then the process 300 may return to step 308 where a new frame of data may be acquired from the scanner 102. At this point, the newly derived three-dimensional data may be fitted to three-dimensional data previously derived in the recover mode. In this manner, a new three-dimensional model may be created within the recover mode. When a successful test fit is made to the original (acquisition mode) three-dimensional model, the entire new three-dimensional model, or a selected portion thereof, may be registered to the original three-dimensional model using a transformation based upon the successfully fitted frames or three-dimensional images.

It will be appreciated that the above steps may be varied, such as by using optical flow techniques to determine correspondence between pixels in adjacent image sets in step 212, and that the order of steps may be changed, such as by providing manual inputs to stop, start, or restart (recover) a scan that override the sequence of steps depicted in FIG. 2, or by performing derivation and test-fitting steps together. As another example, the reference frame selection process may be automated by, for example, capturing a scan from a region of a subject where data has been previously acquired, and registering the newly captured scan to the acquired three-dimensional model. At this point, selection of subsequent reference frames for test fitting and/or fitting may be based upon image sets captured from around the registered location of the newly acquired data. Additionally, certain steps may be added or omitted, or multiple steps may be combined. Similarly, in certain computing environments some steps may be performed in parallel (such as test fitting to multiple reference frames), or certain steps may be distributed among more than one process or processor. In one variation, the scanner may remain in a fixed position, and three-dimensional image capture may be performed by moving the subject within an image plane of the scanner. All such variations and modifications are intended to fall within the scope of this disclosure.

It will be appreciated that the above process may be realized in hardware, software, or any combination of these suitable for the three-dimensional imaging techniques described herein. The process may be realized in one or more microprocessors, microcontrollers, embedded microcontrollers, programmable digital signal processors or other programmable device, along with internal and/or external memory. The process may also, or instead, include an application specific integrated circuit, a programmable gate array, programmable array logic, or any other device that may be configured to process electronic signals. It will further be appreciated that the process may be realized as computer executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. At the same time, processing may be distributed across the camera and/or computer in a number of ways, or all of the functionality may be integrated into a dedicated, standalone image capture device. All such permutations and combinations are intended to fall within the scope of the present disclosure.

It will also be appreciated that means for performing the steps associated with the processes described above with reference to FIGS. 2 and 3 may include any suitable components of the image capture system 100 described above with reference to FIG. 1, along with any software and/or hardware suitable for controlling operation of same. The following figures describe the systems and methods disclosed herein with reference to a user interface that might be rendered, for example, within the display 110 of the image capture system 100 of FIG. 1.

Figure 4:
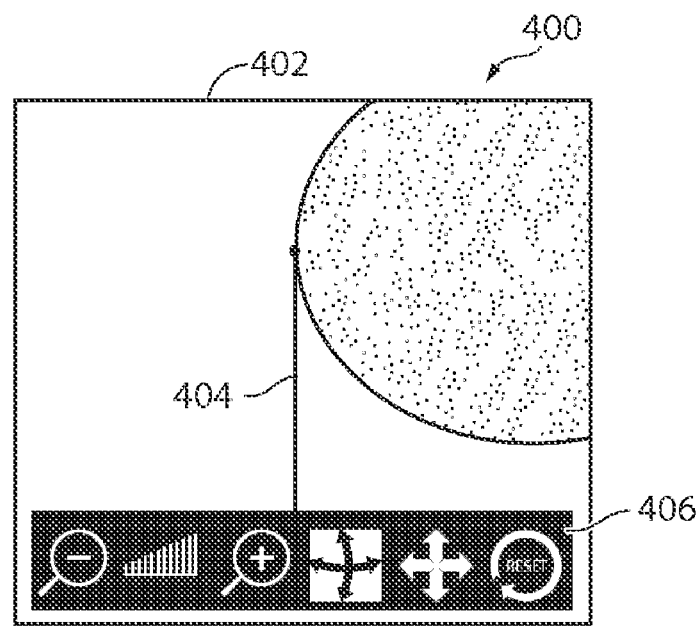
FIG. 4 depicts a view of a user interface for an image capture system.

FIG. 4 depicts a view of a user interface for an image capture system. The user interface 400 may include a window 402 rendered on a monitor such as the display 110 of FIG. 1. Within the window 402, a video image may be displayed including a field of view of a scanner, such as the scanner 102 of FIG. 1. Within the field of view, a subject 404, such as the subject 104 of FIG. 1 may be displayed, along with one or more user controls 406. FIG. 4 specifically depicts the user interface before any image acquisition steps. As such, there is no rendering of an acquired three-dimensional model or any superposition of reference images onto the current video image.

The user controls 406 may generally include one or more controls for manipulating the three-dimensional model (e.g., rotating, scaling, panning, and the like), selecting a landing target, controlling operation of the image capture system (e.g., starting or stopping an acquisition), and so forth. The one or more controls may be manipulated, for example, using any of the user input devices described above with reference to FIG. 1, including physical interaction with the monitor, where the display 110 includes a touch screen.

Figure 5:
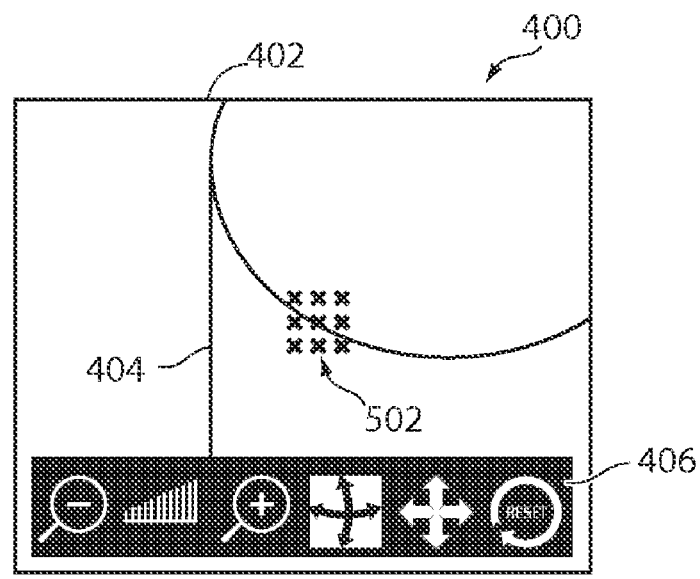
FIG. 5 depicts a view of a user interface for an image capture system in an acquisition mode.

FIG. 5 depicts a view of a user interface for an image capture system, such as described above with reference to FIG. 4, in acquisition mode. In this view, an initial acquisition of a three-dimensional image 502 consisting of a set of three-dimensional points has occurred. The three-dimensional image, a first element of a three-dimensional model, may be rendered within the user interface as superimposed on the video image of the subject 104, as depicted by a number of X's in FIG. 5. It will be appreciated that, while shown as X's for purposes of distinguishing from subsequent three-dimensional images, these points may, in practice, be rendered simply as points or pixels within the user interface. In such a rendering, techniques such as shading of pixels in accordance with simulated lighting may be used, or any other techniques that provide visual cues to contours of the captured three-dimensional points so that a human viewer can more readily interpret the three-dimensional shape captured by the scan.

Figure 6:
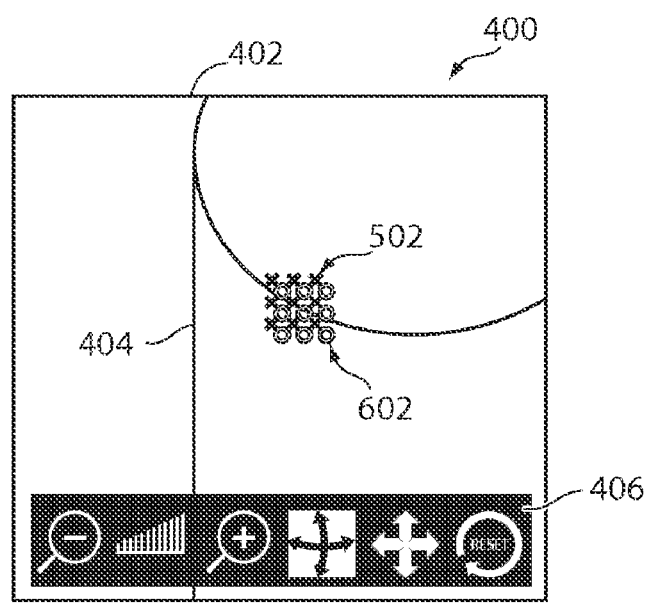
FIG. 6 depicts a view of a user interface for an image capture system in an acquisition mode.

FIG. 6 depicts a view of a user interface for an image capture system, such as described above with reference to FIGS. 4-5, in acquisition mode. In this view, a second acquisition of a three-dimensional image 602 consisting of a set of three-dimensional points has occurred. The second set of three-dimensional points in this view have been successfully fitted to the first three-dimensional image 502 and added to a three-dimensional model. It will be appreciated that, while shown as O's for purposes of distinguishing from other three-dimensional images, these points may, in practice, be rendered simply as points or pixels within the user interface. Over a number of successive acquisitions and fits, a large three-dimensional model may be acquired, and the aggregate point cloud may be rendered with shading to simulate a three-dimensional view of the point cloud, all of which may be superimposed on a current video image of the subject.

Figure 7:
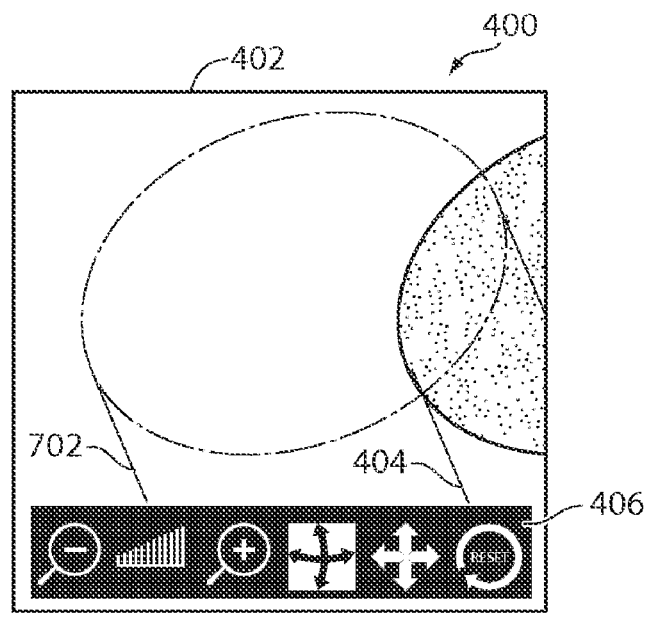
FIG. 7 depicts a view of a user interface for an image capture system in a recover mode.

FIG. 7 depicts a view of a user interface for an image capture system, such as described above with reference to FIGS. 4-6, in a recover mode. In this view, scan acquisition has been lost, such as due to a failure to derive adequate three-dimensional data or a failure to fit a new three-dimensional image to a three-dimensional model. To indicate to a user that the system is in a recover mode, a number of visual cues may be provided. For example, as depicted in FIG. 7, three-dimensional points 502, 602 for the model may be omitted. As another example, a previous video image 702 of the subject may be superimposed on a current video image 404 of the subject. Each image 702, 404 may be rendered in a different color or opacity to indicate its nature. Navigation information is provided in this format. For example, in order to align the current video image 404 with the previous video image 702, a user may move the scanner to the right, thus shifting the current video image 404 of the subject to the left and into alignment with the previous video image 702. The previous video image 702 may be selected as described generally above with reference to FIG. 3 according to its relationship to one or more reference frames for re-acquisition of a scan. In general, when the previous video image 702 and the current video image are aligned (including scaling and rotation), a newly acquired image set or three-dimensional image should successfully fit to one of the reference frames, or have an elevated probability of successfully fitting to one of the reference frames. It will be appreciated that FIG. 7 may also, or instead, depict a landing mode in which a user seeks to reacquire a scan for a stored three-dimensional model.

Figure 8:
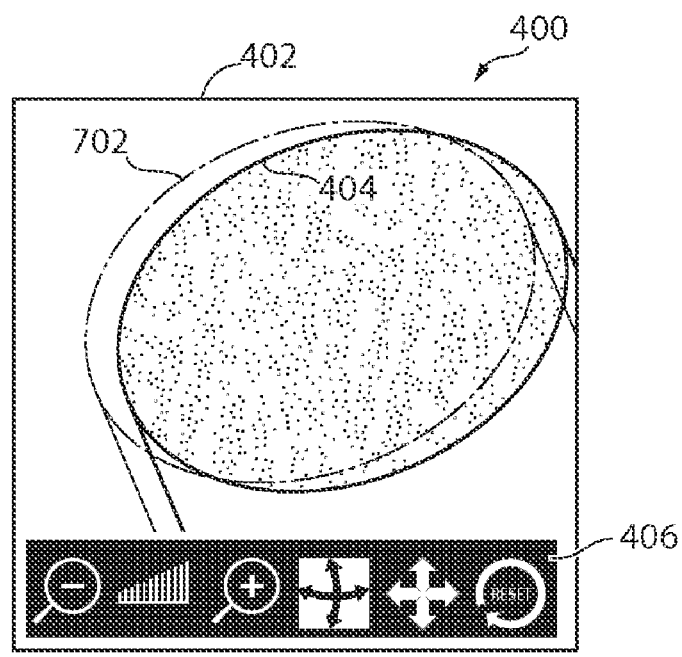
FIG. 8 depicts a view of a user interface for an image capture system in a recover mode.

FIG. 8 depicts a view of a user interface for an image capture system, such as described above with reference to FIGS. 4-7, in a recover mode. FIG. 8 provides a general comparison to FIG. 7, in which a user has manipulated a scanner to more closely align the current video image 404 to the previous video image 702. It will be appreciated that FIG. 8 may also, or instead, depict a landing mode in which a user seeks to reacquire a scan for a stored three-dimensional model.

Figure 9:
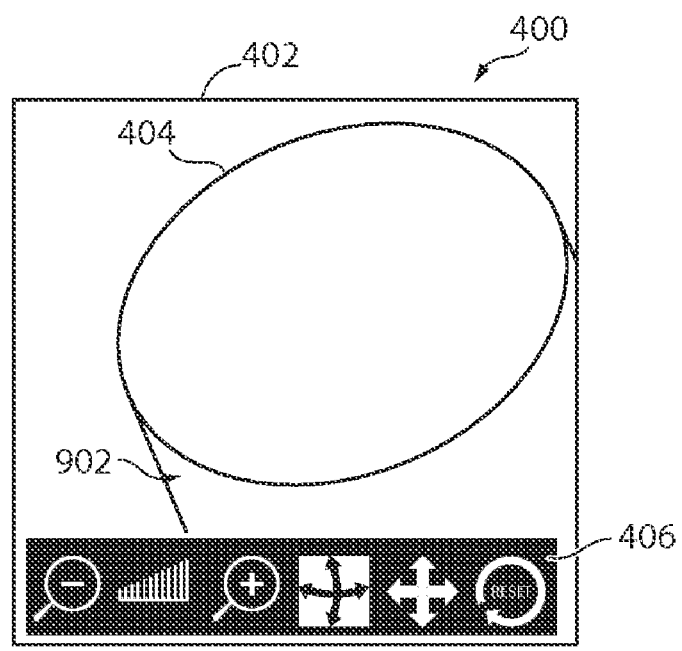
FIG. 9 depicts a view of a user interface for an image capture system after reacquiring a scan.

FIG. 9 depicts a view of a user interface for an image capture system, such as described above with reference to FIGS. 4-8, after reacquiring a scan. In this figure, a user has realigned the current video image 404 so that a newly acquired three-dimensional image could be successfully fitted to one of the reference images. Upon thus exiting the recover mode, the system returns to acquisition mode and begins acquiring additional three-dimensional data to add to the three-dimensional model. The point cloud 902 of the three-dimensional model, optionally including data acquired during the recover mode, is superimposed on the current video image 404 to communicate reacquisition to a user. This visualization also lets the user know where scanning has been performed and where additional scanning may be appropriate.

In other embodiments, a landing mode may be provided in which a user attempts to initiate a new scan registered or connected to an existing three-dimensional model. In the landing mode, the system may optionally create a supplemental three-dimensional model by fitting sequential frames to one another before a successful fit to the original three-dimensional model. In various embodiments, the landing mode may also be distinguished by a user's ability to select a point on the original three-dimensional model for re-acquisition of a scan.

In one aspect, the systems and methods described herein improve real time scanning operations by providing real time user feedback concerning loss and reacquisition of a scan. In another aspect, the systems and methods described herein may be employed in combination with stored three-dimensional models to enhance the functionality of an image capture system. A number of examples of such enhanced functionality are described below.

In one embodiment multiple scans of an object, including scans taken at different times, may be interpreted as a single scan. For example, in a dental application, a tooth surface may be scanned before and after a surface preparation for dental prosthetic. By starting the second, post-preparation scan, by reacquiring a scan of an unprepared tooth surface, the pre-scan and post-scan structure of the prepared surface may be combined into a single surface representation that encloses a space to be filled by the dental prosthetic.

In another embodiment, the user interface may be modified to permit reorientation of the scanner. This may be particularly useful in dental applications where a full dental arch scan might be most conveniently performed in two halves, with a user changing hands or scanner orientation around the midpoint of the arch. The scan could be deliberately interrupted, either by rapidly pulling the remote sensor away from the teeth to affect a stitch loss, or by pressing a "pause" button which may be any of the user input devices described above. At this point, a user may reorient the scan, including one or more reference images, by 180 degrees (or some other amount) within the user interface. This may rotate the system coordinates both for the purposes of display and image correlation in the stitch recovery mode. The operator may then rotate the scanner 180 degrees and attempt to recover a stitch using the recover mode described above. Once the stitch is recovered, the scan can proceed in the normal fashion to capture the remaining teeth.

In another embodiment, the user interface may be modified to permit selection of a point or region of a subject where reacquisition is to be attempted. The interface may, for example, display a point cloud for the three-dimensional model, which a user may rotate, translate, or scale within the interface. A control, which may be accessible using a mouse, keyboard, input device on the scanner, or through a touch screen display, may be provided to select a point or area for recovery of the scan. Using a selection process as described generally above, one or more reference frames may be selected according to spatial or temporal proximity to the selected point, or according to any other suitable selection criteria. Reference frames, image sets, or three-dimensional data may then be selected from historical scan data according to the user selection. After completion of the selection process, a user may enter the recover mode and attempt to recover a lost stitch using the techniques described above.

In another embodiment, the techniques described herein may be applied to allow scanning of complex, articulated, closed, or otherwise difficult surfaces with a scanning device that acquires three-dimensional data as a continuous sequence of three-dimensional images. An application of this is illustrated below with reference to a pair of articulated dental arches.

Figure 10:
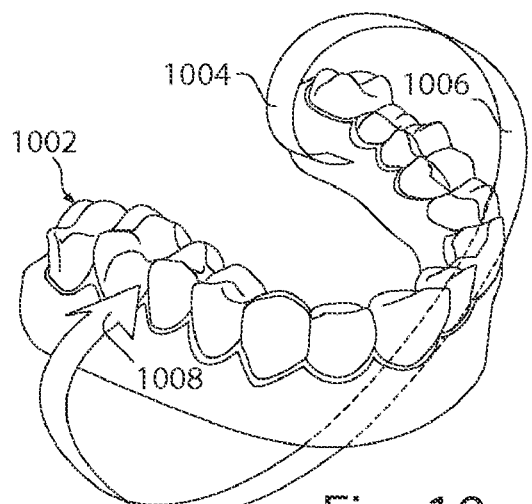
FIG. 10 is a three-dimensional view of a first component of a scanning subject.

FIG. 10 is a three-dimensional view of a first component of a scanning subject. The first component 1002 is viewed here in isolation, i.e., separate from a second component (not shown) that relates to the first component 1002. The first component 1002 in this example is a lower arch of human dentition, including surrounding soft tissue. The objective of a scan may be to acquire a surface map of lower and upper arches of dentition in occlusion. A scan of the arch using the image capture system 100 described above may include a continuous scan of exposed tooth surfaces from within a dental patient's mouth, choosing any convenient location 1004 as a starting point, and continuing in a scan path 1006 that passes over any exposed regions, and concluding at another location 1008 on the exterior surface. At this point, the scan may be manually terminated, or terminated through a manipulation such as moving the scanner rapidly outside of scanning range for the first component 1002. According to one of the embodiments of the recover mode described above, one or more reference frames may be established at the end of this scan. By scanning the exposed surfaces, a complete three-dimensional surface scan of the first component 1002, the lower arch, may be acquired. At the same time, a convenient reacquisition point may be established by forcing the system into recovery mode at a desired location. It will be appreciated that, while the scan path 1006 as illustrated passes below the arch, which would be appropriate for a dental model, a live scan of a patient's dentition captured intraorally would typically only pass over exposed surfaces.

Figure 11:
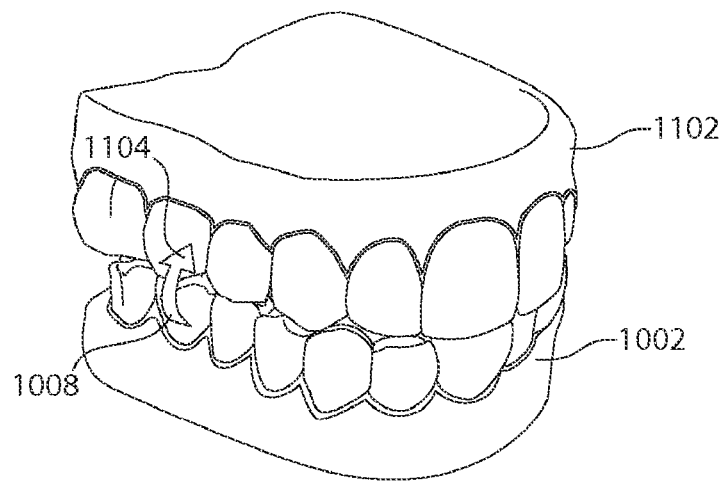
FIG. 11 is a three-dimensional view of a first and second component of a scanning subject.

FIG. 11 is a three-dimensional view of a first and second component of a scanning subject. The first component 1002 may be the lower arch of FIG. 10. The second component 1102 may an upper arch in occlusion with the lower arch. Initiating a second scan from the recover mode, the scan may be reacquired around the location 1008 on the lower arch where the first scan was terminated. The scan may then be continued onto a location 1104 on the second component, where the scan may once again be terminated in recover mode.

Figure 12:
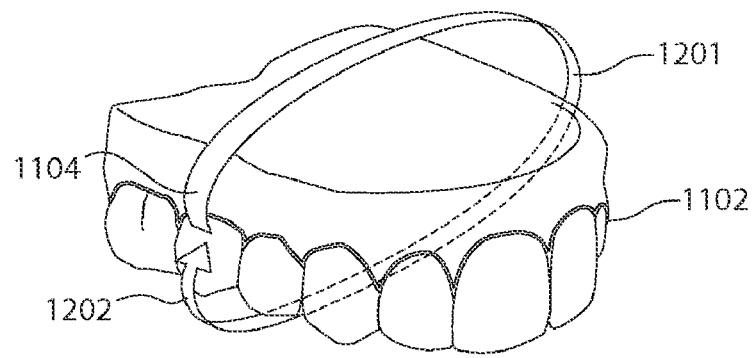
FIG. 12 is a three-dimensional view of a second component of a scanning subject.

FIG. 12 is a three-dimensional view of a second component of a scanning subject. FIG. 12 depicts the second component 1102 in isolation. An arrow 1201 illustrates a third scan beginning at the location 1104 where the scan was previously terminated. The scan may be reacquired at this location 1104 from within the recover mode. After stitch recovery, the scan may be completed of some or all of the second component 1102, ending at a location 1202 on the surface thereof. While depicted generally as encircling the second component 1102, it will be appreciated that a surface scan such as an intraoral scan of human dentition would typically only be possible for exposed surfaces. Scanning in this manner, a complete, three-dimensional surface map may be obtained for the upper arch and lower arch in occlusion may be obtained from a series of intraoral scans of human dentition. This digital version of a dental bite registration may be useful in the fabrication of dental prosthetics involving one or more occluded tooth surfaces. More generally, this technique may be suitably adapted to a number of scanning environments. For example, this technique may be applied to obtain a full three-dimensional surface scan of the interior and exterior of a closed box with a lid, or any other components that may be separated for access to interior regions.

While the technique described with reference to FIGS. 10-12 takes advantage of a recover mode that selects reference frames from an area where stitching was lost, it will be appreciated that a number of adaptations and variations are possible. For example, in one embodiment test fitting in the recover mode may be performed for the beginning and the end of a scan for which acquisition has been lost. Using such a recover mode, the technique may begin with a scan that spans two objects in fixed relationship, starting on the first object and ending on the second object. When the objects are separated, two separate recoveries may be initiated from the beginning and the end of the initial scan. In another embodiment, a user interface that permits selection of a point for reference frames may be employed to permit a number of different scan orders provided at least one scan spans both objects in their desired orientation. In a further variation, any number of separate objects may be sequentially or otherwise scanned in one or more orientations by straightforward extension of the techniques described above. Thus there is disclosed herein systems and methods for scanning a plurality of objects, which may be rigid bodies, in a fixed orientation relative to one another.

While the invention has been disclosed in connection with certain preferred embodiments, other embodiments will be recognized by those of ordinary skill in the art, and all such variations, modifications, and substitutions are intended to fall within the scope of this disclosure. Thus, the invention is to be understood with reference to the following claims, which are to be interpreted in the broadest sense allowable by law.

What is claimed is:

1. A method comprising:
    acquiring three-dimensional surface data from a subject as a sequence of three-dimensional images at a frame rate, each one of the sequence of three-dimensional images fitted to at least one previous one of the sequence of three-dimensional images;
    acquiring an image set for a next three-dimensional image at the frame rate;
    when the image set can be converted into the next three-dimensional image and the next three-dimensional image can be fitted to the three-dimensional surface data, superimposing the three-dimensional surface data and the next three-dimensional image onto a two-dimensional image of the subject in a display; and
    when the image set cannot be converted into the next three-dimensional image or the next three-dimensional image cannot be fitted to the three-dimensional surface data, entering a recover mode comprising the steps of:
        superimposing a current two-dimensional image of the subject onto a previous two-dimensional image of the subject in the display at the frame rate, the previous two-dimensional image representing a view of the subject from a position from which one of the sequence of three-dimensional images was acquired, and the current two-dimensional image representing a view of the subject from a position from which the image set was acquired;
        acquiring at least one subsequent three-dimensional image; and
        test fitting the at least one subsequent three-dimensional image to one or more of the sequence of three-dimensional images.

2. The method of claim 1 further comprising adding the next three-dimensional image to the three-dimensional surface data when the image set can be converted into the next three-dimensional image and the next three-dimensional image can be fit to the three-dimensional surface data.

3. The method of claim 1 wherein the previous two-dimensional image and the current two-dimension image include video frames.

4. The method of claim 1 further comprising manually entering the recover mode in response to a user input.

5. The method of claim 1 further comprising automatically entering the recover mode in response to a detection of a lost acquisition.

6. The method of claim 5 wherein the detection of the lost acquisition includes a detection of a motion blur.

7. The method of claim 5 wherein the detection of the lost acquisition includes a detection of an insufficient recovery of three-dimensional data.

8. The method of claim 1 wherein the recover mode includes the step of highlighting a region on the subject for attempting a recovery.

9. The method of claim 8 wherein the region includes a plurality of previous ones of the sequence of three-dimensional images.

10. The method of claim 1 wherein the recover mode includes the step of test fitting the at least one subsequent three-dimensional image to one or more additional images acquired during the recover mode and test fitting includes selecting a reference image from the sequence of three-dimensional images based on a suitability for test fitting.

11. The method of claim 10 further comprising determining the suitability for test fitting based upon an entropy of image data in the previous three-dimensional image.

12. The method of claim 10 further comprising determining the suitability for test fitting based upon an amount of three-dimensional data in the previous three-dimensional image.

13. The method of claim 10 further comprising determining the suitability for test fitting based upon a placement of three-dimensional data within a range and a field of view of an imaging device.

14. The method of claim 10 further comprising determining the suitability for test fitting based upon a temporal proximity of the at least one subsequent three-dimensional image to one or more of the sequence of three-dimensional images.

15. The method of claim 10 further comprising determining the suitability for test fitting based upon a spatial proximity of the at least one subsequent three-dimensional image to one or more of the sequence of three-dimensional images.

16. The method of claim 1 wherein the recover mode includes the step of manually selecting one or more of the sequence of three-dimensional images.

17. The method of claim 1 wherein the recover mode includes selecting a reference image from a beginning or an end of the sequence of three-dimensional images.

18. A method comprising:
providing three-dimensional surface data for a subject;
acquiring an image set for a three-dimensional image of the subject at a frame rate;
when the image set cannot be fitted to the three-dimensional surface data, entering a landing mode comprising the steps of:
superimposing a current two-dimensional image of the subject onto a previous two-dimensional image of the subject in the display at the frame rate, the current two-dimensional image representing a view of the subject from a position from which the image set was acquired, and the previous two-dimensional image representing a view of the subject from which at least a portion of the three-dimensional surface data was acquired;
acquiring at least one subsequent three-dimensional image at the frame rate;
fitting the at least one subsequent three-dimensional image to a second three-dimensional surface reconstruction;
test fitting the at least one subsequent three-dimensional image to the three-dimensional surface data; and
when the image set can be fitted to the three-dimensional surface data, superimposing the three-dimensional surface data and the next three-dimensional image onto a two-dimensional image of the subject in a display at the frame rate and adding the second three-dimensional surface reconstruction to the three-dimensional surface data.

19. The method of claim 18 wherein the previous two-dimensional image and the current two-dimension image include video frames.

20. The method of claim 18 further comprising manually entering the landing mode in response to a user input.

21. The method of claim 18 further comprising, in the landing mode, highlighting a region on the subject for attempting a landing.

22. The method of claim 21 wherein the region includes a portion of the three-dimensional surface data.

23. The method of claim 18 wherein test fitting includes selecting a reference image from the three-dimensional surface data based on a suitability for test fitting.

24. The method of claim 23 wherein the suitability is based on an entropy of image data in the previous three-dimensional image.

25. The method of claim 23 wherein the suitability is based on an amount of three-dimensional data in the previous three-dimensional image.

26. The method of claim 23 wherein the suitability is based on a placement of three-dimensional data within a range and a field of view of an imaging device.

27. The method of claim 23 wherein the suitability is based on a spatial proximity of the image set to a portion of the three-dimensional surface data.

28. The method of claim 18 further comprising manually selecting a region of the three-dimensional surface data for test fitting.

29. The method of claim 18 wherein test fitting includes selecting a reference image from a beginning or an end of a sequence of three-dimensional images used to construct the three-dimensional surface data.

30. The method of claim 18 further comprising manually entering a recover mode in response to a user input.

31. The method of claim 18 further comprising manually selecting a region from the three-dimensional surface data for test fitting.

32. A system comprising:
a scanning device that acquires three-dimensional surface data from a subject as a sequence of three-dimensional images at a frame rate, each one of the sequence of three-dimensional images fitted to at least one previous one of the sequence of three-dimensional images, the device including an acquisition mode in which one or more additional three-dimensional images are acquired and added to the three-dimensional surface data at the frame rate, and the device including a recovery mode in which one or more additional three-dimensional images are test fit to one or more of the sequence of three-dimensional images to recover the acquisition mode; and
a display adapted to provide one or more visual indicators distinguishing between the acquisition mode and the recovery mode, wherein during the recovery mode the display shows, at the frame rate, a current two-dimensional image from the scanning device and a two-dimensional image from a point of view corresponding to one of the sequence of three-dimensional images.

33. The system of claim 32, the display further adapted to provide guidance to an operator in the recovery mode in manipulating the scanning device to recover the acquisition mode.

* * * * *